United States Patent [19]

Evers

[11] 4,020,175

[45] Apr. 26, 1977

[54] CERTAIN 3-FURYL SULFIDES

[75] Inventor: William John Evers, Long Branch, N.J.

[73] Assignee: International Flavors & Fragrances Inc., New York, N.Y.

[22] Filed: Oct. 10, 1972

[21] Appl. No.: 295,859

Related U.S. Application Data

[63] Continuation of Ser. No. 864,227, Oct. 6, 1969, abandoned, which is a continuation-in-part of Ser. No. 796,923, Feb. 5, 1969, Pat. No. 3,666,495.

[52] U.S. Cl. .......................................... 260/347.2
[51] Int. Cl.$^2$ ..................................... C07D 307/64
[58] Field of Search ............................... 260/347.2

[56] References Cited

UNITED STATES PATENTS 3,394,016   7/1968   Bidmead et al. ................... 426/65

FOREIGN PATENTS OR APPLICATIONS 946,441   8/1959   Germany

OTHER PUBLICATIONS

Mayer et al., Angew. Chem. International Edit. (1964), vol. 3/No. 4, pp. 277–286.

*Primary Examiner*—Henry R. Jiles
*Assistant Examiner*—Bernard Dentz
*Attorney, Agent, or Firm*—Brooks Haidt Haffner & Delahunty

[57] ABSTRACT

Novel 3-sulfur derivatives of furan including alkyl furan-3-thiols and bis(alkyl-3-furyl) sulfides and di- and tetrahydro derivatives thereof having meaty and/or roasted aromas and flavors; processes for producing such 3-sulfur derivatives; novel flavoring compositions containing such derivatives; and novel food compositions containing such derivatives.

9 Claims, No Drawings

CERTAIN 3-FURYL SULFIDES

This application is a continuation of application Ser. No. 864,227 filed on Oct. 6, 1969 now abandoned which in turn is a continuation-in-part of U.S. application Ser. No. 796,923 filed Feb. 5, 1969 now U.S. Pat. No. 3,666,495.

Artificial flavoring agents for foodstuffs have received increasing attention in recent years. In many areas, such food flavoring agents are preferred over natural flavoring agents, at least in part because of the uniform flavor that may be so obtained. For example, natural food flavoring agents such as extracts, essences, concentrates and the like are often subject to wide variation due to changes in the quality, type, and treatment of the raw materials. Such variation can be reflected in the end product and results in unreliable flavor characteristics and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned goods, sauces, gravies, and the like are apt to be stored by the consumer for some time prior to use.

The fundamental problem in preparing artificial flavoring agents is that of achieving as nearly as possible a true flavor reproduction. This generally proves to be a difficult task since the mechanism for flavor development in many foods is not understood. This is notable in products having meaty and roasted flavor characteristics.

Reproduction of roasted and meat flavors and aroms has been the subject of a long and continuing search by those engaged in the production of foodstuffs. The severe shortage of foods, especially protein foods, in many parts of the world has given rise to the need for utilizing non-meat sources of proteins and making such proteins as palatable and as meat-like as possible. Hence, materials which will closely simulate or exactly reproduce the flavor and aroma of roasted products and meat products are required.

Moreover, there are a great many meat-containing or meat-based foods presently distributed in a preserved from, examples being condensed soups, dry soup mixes, dried meats, freeze-dried or lyophilized meats, packaged gravies, and the like. While these products contain meat or meat extracts, the fragrance, taste, and other organoleptic factors are very often impaired by the processing operations, and it is desirable to supplement or enhance the flavors of these preserved meat foods.

THE INVENTION

The present invention provides novel materials having desirable meat, roast meat, and roasted fragrance and flavor notes. These materials are organic oxygen-containing heterocyclics wherein the second carbon atom from the oxygen atom contains a sulfur substituent. Such materials include furan derivatives having the formula:

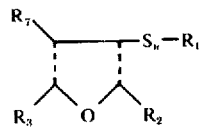

wherein $n$ is one to four; $R_1$ is hydrogen, alkyl, alkenyl, alkadienyl, or a moiety of the formula

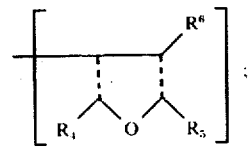

$R_2$, $R_3$, $R_4$, $R_5$, $R_6$, and $R_7$ are hydrogen, alkyl, alkenyl, or alkadienyl, or taken together $R_5$ and $R_6$ and/or $R_3$ and $R_7$ form cyclialkyl, cyclialkenyl, cyclialkadienyl, benzo, thieno, dihydrothieno, tetrahydrothieno, furano, dihydrofurano, or tetrahydrofurano rings; and the dashed lines represent single or double carbon-to-carbon bonds.

The present invention also contemplates flavoring and flavor-enhancing compositions containing the 3-sulfur substituted furan derivatives, and foodstuffs and food compositions containing such furan derivatives. The methods for preparing such furan derivatives and such food compositions are also contemplated within the present disclosure.

When $R_2$, $R_3$, $R_4$, $R_5$, $R_6$ and $R_7$ represent alkyl, alkenyl, or alkadienyl groups, it is desirable that they be lower alkyl, alkenyl or alkadienyl groups having up to five carbon atoms. Thus, for example, these groups can be methyl, ethyl, propyl, isopropyl, butyl, secondary butyl, pentyl, vinyl, allyl, isopropenyl, butenyl, butadienyl, isopentenyl, pentenyl, pentadienyl, isopentadienyl, and the like. When $R_5$ and $R_6$ and/or $R_3$ and $R_7$, taken together form cyclialkyl or cyclialkenyl or cyclialkadienyl rings, it is preferred that they be 5- or 6-membered rings. Thus, for examples, the following fused ring compound is representative of one of such ring materials:

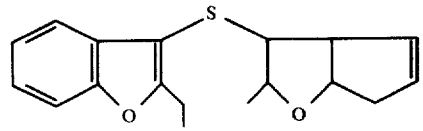

The particularly preferred materials according to the present invention for imparting desirable meat, roast meat, and roasted fragrance and flavor notes include furan derivatives having the formula:

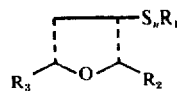

wherein $n$ is one and $R_1$ is hydrogen or $n$ is one, two, three or four and $R_1$ is a moiety of the formula:

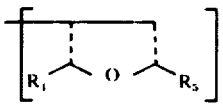

or n is two or three and $R_1$ is alkyl, and wherein $R_2$ and $R_4$ are alkyl, $R_3$ and $R_5$ are hydrogen or alkyl, and the dashed lines represent single or double carbon-to-carbon bonds. In this preferred embodiment, when $R_1$, $R_2$, $R_3$, $R_4$, and $R_5$ represent alkyl groups it is desirable that they be lower alkyl groups having up to five carbon atoms. Thus, the alkyl groups can be methyl, ethyl, propyl, isopropyl, butyl, secondary butyl, pentyl, and the like. It is especially preferred that the alkyl groups be methyl or ethyl.

It has been found that when both dashed lines represent double bonds, that is, when the ring is a furyl ring, the compounds have a desirable pronounced meat flavor and aroma characteristic. When the furan ring is more highly saturated, and particularly when the ring is dihydrofuryl, a roasted flavor and aroma characteristic is more dominant.

The novel compounds of the present invention are oily liquids or crystalline solids and are, in general, characterized by pronounced pleasant meat, roasted meat and/or roasted food flavor and aroma at the levels taught herein. The dominant note is one of roasted protein with a notable absence of any pungency or lachrymose factor.

It will be understood that some of the novel compounds of this invention can exist in various isomeric forms, and the formulas given herein include such isomers. By way of example, the 2-methyl-[2,3H]-dihydrofuran-3 thiols exist as geometric isomers and as optical isomers. A representation of one of the isomers of this compound is as follows:

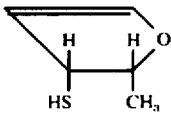

Another isomer is:

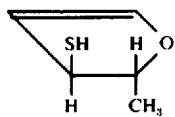

Exemplary of 3-sulfur substituted furans contemplated herein are:
bis-(2-methyl-3-furyl) tetrasulfide
2-methylfuran-3-thiol
2-methyldihydrofuran-3-thiol
2-methyltetrahydrofuran-3-thiol
2-ethylfuran-3-thiol
2-ethyldihydrofuran-3-thiol
2-ethyltetrahydrofuran-3-thiol
2-propylfuran-3-thiol
2-isopropylfuran-3-thiol
2-isopropyldihydrofuran-3-thiol
2-isopropyltetrahydrofuran-3-thiol
2-propyldihydrofuran-3-thiol
2,5-dimethylfuran-3-thiol
2,5-dimethyldihydrofuran-3-thiol
2,5-dimethyltetrahydrofuran-3-thiol
2,5-diethylfuran-3-thiol
2,5-diethyldihydrofuran-3-thiol
2,5-diethyltetrahydrofuran-3-thiol
2-ethyl-5-methylfuran-3-thiol
2-methyl-5-ethylfuran-3-thiol
2-ethyl-5-methyldihydrofuran-3-thiol
2-ethyl-5-methyltetrahydrofuran-3-thiol
2,5-dipropylfuran-3-thiol
2,5-diisopropylfuran-3-thiol
5-isopropyl-2-methylfuran-3-thiol
2-butylfuran-3-thiol
2-ethyl-5-propyltetrahydrofuran-3-thiol
bis(2-methyl-3-furyl) sulfide
bis(2-methyl-3-furyl) disulfide
bis(2-ethyl-3-furyl) sulfide
bis(2-ethyl-3-furyl) disulfide
bis(2,5-dimethyl-3-furyl) sulfide
bis(2,5-dimethyl-3-furyl) disulfide
bis(2-methyl-3-dihydrofuryl) sulfide
bis(2-methyl-3-tetrahydrofuryl) sulfide
bis(2-methyl-3-tetrahydrofuryl) disulfide
bis(2-methyl-3-dihydrofuryl) disulfide
bis(2,5-diethyl-3-dihydrofuryl) sulfide
bis(2,5-diethyl-3-furyl) sulfide
bis(2-ethyl-5-methyl-3-furyl) disulfide
bis(2,5-diethyl-3-furyl) disulfide
bis(2,5-dipropyl-3-furyl) disulfide
bis(2,5-dipropyl-3-furyl) sulfide
bis(2,5-dibutyl-3-furyl) disulfide
bis(5-ethyl-2-methyl-3-dihydrofuryl) disulfide
bis(2-isopropyl-3-furyl) sulfide
bis(2-isopropyl-3-furyl) disulfide
bis(2-isopropyl-3-dihydrofuryl) sulfide
bis(2-isopropyl-3-tetrahydrofuryl) disulfide It will be understood from the present disclosure that the derivatives of dihydrofuran can be 2,3H or 4,5H. Thus, 2-methyldihydrofuran-3-thiol includes 2-methyl[4,5H]-dihydrofuran-3-thiol and 2-methyl-[2,3H]-dihydrofuran-3-thiol, and bis(5-ethyl-2-methyl-3-dihydrofuryl) disulfide includes bis[5-ethyl-2-methyl-3-([4,5H]-dihydrofuryl)] disulfide and bis[5-ethyl-2-methyl-3-([2,3H]-dihydrofuryl)] disulfide.

In accordance with a further aspect of this invention, the novel sulfur compounds are utilized singly, in admixture, or in combination with other edible materials to impart a meaty or roasted organoleptic impression to foods or edible materials. Thus, the compounds herein described can comprise flavoring compositions and flavor-enhancing compositions. It will be understood herein that a flavoring composition is one capable of imparting a definite flavor to a tasteless or bland foodstuff, and a flavor-enhancing composition is one capable of reinforcing one or more flavor notes of a natural or other material which is deficient in flavor. A flavor-enhancing composition would be useful for improving the flavor of, say, a canned meat product, the flavor of which was diminished or undesirably altered by the processing. It will accordingly be understood that the disclosed sulfur-containing compounds can be mixed with other flavoring ingredients, carriers, vehicles and the like to form compositions suitable for imparting a flavor to, enhancing the flavor in, or altering the flavor of, a food composition, and such food compositions and the methods for preparing them are included in this disclosure. The furyl monosulfides, disulfides, and mercaptans of this invention generally impart a meat or cooked meat flavor and aroma. The dihydrofuryl sulfides, disulfides, and mercaptans impart a roasted flavor and odor which is even redolent of roasted sesame seeds in some instances. Their flavor characteristics are sufficiently pronounced and persistent that a desirable flavor and odor can be developed by simply using the undiluted compound or compounds; for example, by addition of the undiluted compound to a processed fish meal.

When the sulfur compounds of this invention are used in flavoring compositions to enhance existing flavors in, or to provide the entire flavor impression to, a foodstuff, they can be combined with organic acids including fatty, saturated, unsaturated and amino acids, alcohols, including primary and secondary alcohols, esters, carbonyl compounds including aldehydes and ketones, lactones, cyclic organic materials including benzene derivatives, alicyclics, heterocyclics such as furans, pyridines, pyrazines and the like, sulfur-containing materials including thiols, sulfides disulfides and the like, proteins, lipids, carbohydrates, and so-called flavor potentiators such as monosodium glutamate, guanylates, inosinates, natural flavoring materials such as vanillin, and the like. It will be appreciated that the types and amounts of materials selected from the foregoing groups of materials will depend upon the precise organoleptic character desired in the finished product and, especially in the case of flavoring compositions used to enhance other flavors, will vary according to the foodstuff to which the flavor and aroma are to be imparted. Inorganic materials such as sodium chloride and freshness preservers such as butylated hydroxyanisole, butylated hydroxytoluene and propyl gallate can be added for their adjuvant to preservative effects on the flavoring composition or on the final food composition itself.

As noted above, it can also be desirable to utilize carriers such as gum arabic and carrageenen or vehicles such as ethyl alcohol, water, propylene glycol. When the carrier is an emulsion, the flavoring composition can also contain emulsifiers such as mono- and diglycerides of fatty acids and the like. With these carriers or vehicles the desired physical form of the composition can be prepared. It will be understood that the compounds of this invention can be used in spray-dried, liquid, encapsulated, emulsified and other forms in which flavorings are added to foodstuffs. The compounds can be so used alone or in combination with the other ingredients set forth therein. In the case of a foodstuff which is prepared from a combination of ingredients the furyl sulfur derivatives, flavor enhancers and flavoring compositions of this invention can be added to one of the ingredients and thereby be incorporated into the composition as a whole.

The amount of novel sulfur-containing compound or compounds used should be sufficient to impart a meaty or roasted flavor and aroma note to the ultimate foodstuff in which they are used. Thus, a small but effective amount of 3-sulfur substituted furan sufficient to provide the meaty flavor note in, or to round out the meat, roasted, or other flavor note in, the ultimate foodstuff is used. The amount will vary depending upon the ultimate food composition to be flavored; for example, more may be required in producing a full, rounded meat flavor in an unflavored material and less may be required when this invention is used to enhance a meat or roasted foodstuff or flavoring material which is deficient in natural flavor or aroma.

Those skilled in the art will appreciate that the amount of furyl sulfur derivatives according to this invention can be varied over a range to provide the desired flavor and aroma. The use of too little of the derivative or derivatives will not give the full benefit, while too much will make the flavor compositions and foodstuffs needlessly costly, and in extreme cases will unbalance the flavor and aroma so that optimum results are not obtained.

It is accordingly preferred that the ultimate food composition contain at least about 1.0 part per billion of the sulfur derivatives, based on total composition, and it is not generally desirable to use more than about 500 parts per million (ppm) in the finished composition. Thus, the desirable range for use in the practice of this invention is from about 0.001 to about 500 ppm of the furyl sulfur compound or compounds. When these compounds are added to the foodstuff in the form of a meat flavor composition, the amount should be sufficient to impart the requisite flavor and/or aroma note to the composition so that the flavor and aroma will be balanced in the finished foodstuff. Accordingly, the flavoring compositions of this invention preferably contain from about 0.0001% to 10% of sulfur derivatives based on the total weight of said flavoring composition. Unless otherwise indicated, all parts, proportions, percentages, and ratios herein are by weight.

The flavoring compositions of this invention can be added to the foodstuffs by conventional methods known in the art. The flavor material of this invention, together with any other liquids if desired, can be admixed with a carrier, such as gum arabic, gum tragacanth, carrageenen and the like, and spray-dried to obtain a particulate solid flavoring material. Where a powdered prepared flavor mix is being made, the dried solids and flavoring compositions or furyl sulfur derivatives of this invention are mixed together in a dry blender to attain uniformity.

When liquid materials are involved in the preparation of foodstuffs, the flavoring materials of this invention can be combined with either the liquid to be used in the finished composition, or alternatively they can be added with a liquid carrier in which they are dissolved, emulsified, or otherwise dispersed.

It has been found that the bis(2,5-diakyl-3-furyl) sulfide can readily be prepared by reacting a 2,5-dialkyl furan with the appropriate sulfur chloride in the presence of a catalyst. Thus, a bis(2,5-dialkyl-3-furyl) sulfide is produced by the reaction of a 2,5-dialkyl furan with sulfur dichloride, $SCl_2$, and a bis(2,5-dialkyl-3-furyl) disulfide can be obtained by the reaction of such a 2,5-dialkyl furan with sulfur monochloride, that is, $S_2Cl_2$.

While the reaction can be carried out in the absence of catalysts, it is preferred to use as catalysts Lewis acids including metal salts such as stannic chloride, ferric chloride, ferric bromide, zinc chloride, boron trifluoride, and boron trifluoride complexes such as boron trifluoride diethyl etherate, and the like.

It has been found that the time of reaction for obtaining suitable results in between 15 minutes and 2 hours; that the desirable temperature range is between $-30°$ and $+50°$ C; that a reaction vehicle is preferable for controlling the reaction; and that such reaction vehicle can be a hydrocarbon solvent such as hexane, cyclohexane, and the like or dimethyl furan used in large excess. The reactant proportions are such that the dimethyl furan compound is used in large molar excess over the particular sulfur chloride. The reaction is preferably run at atmospheric pressure.

It has also been discovered that furan-3-thiols and alkyl-substituted furan-3-thiols can be produced by the reaction of an appropriate dihydrofuranone-3 or tetrahydrofuranone-3 with hydrogen sulfide in the presence of anhydrous hydrogen chloride at temperatures of −60° to −100° C. This reaction provides furan-3-thiols; dihydrofuran-3-thiols; and tetrahydrofuran-3-thiones as well as alkyl-substituted derivatives thereof.

The reaction of the di- or tetrahydrofuranone-3 or alkylated counterparts with hydrogen sulfide in the presence of gaseous hydrogen chloride will take place in from about 5 up to about 25 hours at temperatures of about −60° down to about −100° C. The reaction vehicle can be any polar solvent having a melting point below about −100° C and a viscosity such that the reaction mass can be turbulently mixed at that temperature. Desirable polar solvents having the above properties are Diglyme, tetrahydrofuran, methanol, ethanol and the like. The hydrogen sulfide reactant is preferably in about a 5- to 10-fold excess over the furanone-3.

It will be understood that the thione can readily be converted to the corresponding thiol with a reducing agent such as lithium aluminum hydride, diethoxy aluminum hydride, ethoxy aluminum dihydride and the like. The vehicle for this reduction can be an oxygenated solvent such as diethyl ether, tetrahydrofuran, Diglyme (dimethyl ether of diethylene glycol), and the like. The temperature of the reaction can vary from about 0° C up to the reflux temperature of the reaction medium. Although the reaction can be carried out over a range of pressures, it is preferred that the pressure be atmospheric. The reducing agent is preferably in excess molar proportion relative to the thione.

It will be understood that the corresponding bis(3-furyl) bis(3-dihydrofuryl), and bis(3-tetrahydrofuryl) disulfides can be produced by oxidizing the corresponding thiols under mild oxidizing conditions. Thus, the thiols can be oxidized with an air stream bubbled through them at 20° C and 760 mm Hg pressure for 8 hours. Stirring of the reaction mass with use of baffles during the bubbling is adequate to maintain suitable contact between the reactants. Other suitable mild oxidizing agents include ferric chloride, iodine-potassium iodide, dimethyl disulfide, dimethylsulfoxide and the like.

The time of this mild oxidation reaction will vary from substantially instantaneous up to 20 hours at temperatures from about 10° to 50° C and atmospheric pressure. The pH of the reaction mass depends upon the nature of the oxidizing agent; as does the time of reaction which is a function of the net oxidation reduction potential of the reactants and the concentrations and relative proportions of the reactants. It is preferred that stoichiometric quantities of thiol and oxidizing materials be used unless such easy-to-remove oxidizing agents ad dimethyl sulfoxide, dimethyl sulfide and the like are employed, in which case an excess of such oxidizing agents can be utilized.

In another process contemplated herein a 2-alkyl-5-furoic acid, 2-alkyl-5-cyanofuran, or a 2-alkyl-5-halofuran is treated with oleum (fuming sulfuric acid) to produce the 3-sulfo derivative. When the 5-furoic acid is used, the barium salts of the resulting acid are then obtained by treatment of the acid with barium carbonate which is used in excess so as to eliminate any unreacted sulfuric acid. The barium salt is converted to the sodium salt which is then decarboxylated with an equivalent amount or an excess of mercuric chloride in a refluxing aqueous solution. The resulting sodium sulfonate is reacted with a 7-8 fold excess of thionyl chloride, the excess of thionyl chloride being used as a solvent in the presence of a trace of dimethyl formamide. In place of excess thionyl chloride, other inert solvents may be used, for example, benzene, hexane or diethyl ether. The resulting 3-chlorosulfo group is reduced to the thiol (—SH) group by reaction with a reducing agent used in excess to insure total reduction. Agents such as lithium aluminum hydride, monoalkoxy aluminum dihydride, dialkoxy aluminum hydride or zinc in hydrochloric acid wherein each of these reducing agents is in a vehicle can be used. Such a reduction can be carried out at room temperature to reflux under atmospheric pressure. The vehicle carrying the reducing agent can be oxygenated vehicles such as diethyl ether, tetrahydrofuran, Diglyme, and the like.

Saturated furan-3-thiols can also be produced by treating alkyl-3-halotetrahydrofurans with sodium hydrosulfide under reflux conditions in the presence of ethanol, methanol, or like vehicles. The mercaptans of this invention can, if desired, be reacted with various chlorosulfur compounds to obtain di- or tri- or tetrasulfides. Thus, a thiol such as 2-methyl-3-furan thiol can be reacted with an equimolar amount of methyl disulfur chloride, $CH_3S_2Cl$, at a temperature of from −60° C up to about 0° C to produce methyl(2-methyl-3-furyl) trisulfide. This reaction can be carried out in a solvent such as diethyl ether, cyclohexane, hexane, carbon tetrachloride, benzene and the like. Similarly, a thiol such as 2-methyl-3-furanthiol can be reacted with an equimolar amount of methanesulfenyl chloride, $CH_3SCl$, to produce methyl(2-methyl-3-furyl) disulfide. This reaction also can be carried out in a solvent such as diethyl ether, cyclohexane, hexane carbon tetrachloride, benzene and the like. The reaction temperature is preferably from −60° C up to 0° C at atmospheric pressure.

The di- and tetrahydro materials according to this invention are also conveniently prepared directly from the appropriate alkyl or di- or tetrahydrofurans, under reaction conditions similar to the conditions used in the analogous reaction described heretofore.

The bis(2-methyl-3-furyl) disulfide and 2-methyl-3-furan thiol of this invention can also be obtained by: (a) forming a mixture of thiamine, cysteine, hydrolyzed vegetable protein and water and heating the mixture to reflux for a period of from about 2 to about 10 hours as shown in U.S. Pat. No. 3,394,016; (b) removing the distillate at intervals; (c) treating the distillate in an extractive process using as an extractant a low boiling solvent such as methylene chloride and the like, whereby the bis(2-methyl-3-furyl) disulfide and 2-methyl-3-furan thiol of this invention are obtained; (d) separating the furyl sulfur compounds from the mixture by means of, for example, a gas-liquid chromatographic column or column chromatographic techniques.

The following examples are given to illustrate embodiments of the invention as it is presently preferred to practice it. It will be understood that these examples are illustrative, and the invention is not to be considered as restricted thereto except as indicated in the appended claims.

EXAMPLE I

Preparation of bis(2,5-Dimethyl-3-furyl) sulfide and bis(2,5-Dimethyl-3-furyl) disulfide Into a 1-liter, three-neck, round bottom flask equipped with addition funnel and magnetic stirrer are introduced 175 g of 2,5-dimethylfuran and 0.4 g of stannic chloride. After cooling to −20° C 75.3 g of sulfur dichloride, $SCl_2$, is added during 33 minutes while maintaining a temperature of −20° C. The reaction mixture is stirred for 1 hour and 40 minutes and allowed to warm to +34° C. Pouring the reaction mixture into 1 liter of ice-water, and extraction with hexane gives, after drying with sodium sulfate and solvent removal, 64.8 g of residue. Column chromatography of the residue on 1625 g of silicic acid with 5% diethyl ether in hexane gives 14.4 g of a mixture of mono- and disulfides. Distillation of 11.0 g of mixture provides 3.8 g of bis(2,5-dimethyl-3-furyl) sulfide, b.p. 81°–85° C at 0.15 mm Hg, and 5.1 g of bis(2,5-dimethyl-3-furyl) disulfide, b.p. 112°–116° C at 0.45 mm Hg.

Repeating the above experiment using 98.5 g of sulfur monochloride, $S_2Cl_2$, in place of sulfur dichloride produces a 54.2 g residue. Chromatography on 1355 g of silicic acid with 5% ether in hexane yields 13.9 g of mono- and disulfide. Distillation of 11.0 g of the mixture gives 1.96 g of a 40/60 mixture, as determined by proton magnetic resonance (PMR) of mono- and disulfide and 6.6 g of bis(2,5-dimethyl-3-furyl) disulfide, b.p. 115° C at 0.45 mm Hg.

The data on the bis(2,5-dimethyl-3-furyl) sulfide are as follows:

Proton Magnetic Resonance
In carbon tetrachloride:
  2.2 (singlet, 6 protons)
  2.3 (singlet, 6 protons) and
  5.78 (singlet, 2 protons) ppm.

Infra-red:

| $\lambda$max. | Interpretation |
|---|---|
| 3.22 | CH stretch of aromatic ring |
| 6.21, 6.36 | C=C stretch of aromatic furan ring |
| 7.26 | Methyl group |
| 12.05 | CH bond of aromatic ring. |

Mass Spectrum

| Ratio of Mass to Charge | Net Peak Height | Pattern Intensity % |
|---|---|---|
| 43 | 1100. - | 100.01 |
| 53 | 130. - | 11.8 |
| 95 | 140. - | 12.7 |
| 96 | 280. - | 25.56 |
| 126 | 390. - | 35.53 |
| 127 | 310. - | 28.25 |
| 128 | 220. - | 20.0 |
| 179 | 320. - | 29.14 |
| 207 | 210. - | 19.1 |
| 222 | 800. - | 72.72 |

Both compounds impart a distinct meaty flavor to a soup base at a concentration of 0.2 ppm. The bis(2,5-dimethyl-3-furyl) disulfide is preferred and both 3-furyl sulfides are preferred over bis(5-methyl-2-furyl) disulfide which is found to have only a chemical, rubbery taste and aroma under the same conditions.

EXAMPLE II

Preparation of bis(2,5-Dimethyl-3-furyl) Monosulfides.

Into a 25 ml three-neck, round-bottom flask equipped with an addition funnel, magnetic stirrer and ice bath are introduced 9.6 g of 2,5-dimethylfuran and 1.104 g of stannic chloride. At a temperature of 0° C 2 g of sulfur dichloride, $SCl_2$, is added during 33 minutes. The reaction mixture is then poured into 50 cc of ice-water slurry, and the reaction mass is extracted twice with 20 cc of isopentane and once with 40 cc of diethyl ether. About three grams of brown oil is recovered after solvent removal. This brown oil has an odor of roast meat. Column chromatography on 50 g of silicic acid with 5% ether in hexane gives 0.6 g of material having a roast meat aroma. Rechromatography of this material on 25 g of silicic acid initially using hexane and then 1% ether in hexane as eluent gives 0.22 g of a mixture of 2,5-dimethyl-3-furyl monosulfide and 2,5-dimethyl-3-furyl disulfide.

The resulting mixture of bis(2,5-dimethyl-3-furyl) sulfide and disulfide is recovered after the combined solvent extracts have been evaporated. The sulfide and disulfide have a meat aroma and a cooked meat taste.

EXAMPLE III

Preparation of bis(2,5-Dimethyl-3-furyl) Disulfide

Into a 500 cc three-neck, round bottom flask equipped with a thermometer and addition funnel, and immersed in an acetone-dry ice bath are added: 78.6 g 2,5-dimethylfuran, 0.1 g anhydrous stannic chloride, and 100 cc hexane. Over a period of one hour, 27 cc of sulfur monochloride, $S_2Cl_2$, is added while the pot temperature is maintained between −22° and 0° C. During the last 20 minutes a vacuum is applied to the reaction flask to remove the hydrogen chloride gas which evolves.

At the end of the reaction the reaction mass is poured onto 200 cc of a water-ice slurry. Hexane-insoluble solids are then filtered and the aqueous layer is separated from the hexane layer. The hexane layer is washed with one volume of 10% aqueous sodium bicarbonate and then with 100 cc of water. This is followed by washes with 200 cc water, 5% aqueous sodium carbonate and 200 cc water. The hexane solution is then dried over anhydrous sodium sulfate and filtered, and the hexane is evaporated to produce 21.9 g of a dark oil. This dark oil, on standing, deposits a solid. The residual oil is taken up in 50 cc hexane and the hexane solution is washed twice with 50 cc and once with 100 cc of water. After drying over sodium sulfate and solvent removal, 11.4 g of oil is recovered.

Ten grams of this crude oil is dissolved in 5% of diethyl ether in hexane and subjected to column chromatography using a 5.5 × 78 cm column packed with 200 g of silicic acid and the diethyl ether-hexane mixture as eluent. Analysis of the 5.3 g of product recovered from the column by means of proton magnetic resonance and infra-red and mass spectroscopy confirms the production of bis(2,5-dimethyl-3-furyl) disulfide. This material has a roasted-meat aroma and a cooked-meat taste.

Analytical data are obtained as follows:

Infra-red:

-continued

| λmax | Interpretation |
|---|---|
| 3.22 | Aromatic CH stretch |
| 6.21, 6.38 | Aromatic ring C=C stretch |
| 7.23 | Methyl group |
| 12.55 | CH bond of aromatic ring |

Proton Magnetic Resonance:
In carbon tetrachloride:
 2.1 (singlet, 6 protons),
 2.27 (singlet, 6 protons), and
 6.0 ppm (singlet, 2 protons).
Mass Spectrum:
Base Peak 43, Molecular Peak 254. Other peaks in descending order: 127, 128, 85.

EXAMPLE IV

Production of Furan-3-Thiol Derivatives

A 250 ml flask fitted with a mechanical stirrer, gas inlet tube, calcium chloride drying tube, thermometer, and Y-tube is charged with 50 ml of distilled Diglyme, and the Diglyme is saturated with gaseous hydrogen chloride at 0°–5° C with constant stirring.

The flask is then immersed in a dry ice-isopropanol bath at −80° C. The cooled flask is charged with 14.0 g (0.14 mole) of 2-methyl-3-tetrahydrofuranone, and 28.5 g (0.84 mole) of hydrogen sulfide which has been chilled to −80° C is slowly warmed and allowed to boil over into the reaction flask.

About one-half hour after the beginning of the hydrogen sulfide addition a pink-red color begins to appear in the reaction mixture. by the end of the 2.5 hours required for the addition of all the hydrogen sulfide, the reaction mixture is orange in color. At this time stirring is stopped, and the reaction mixture is permitted to stand 16 hours.

A 1-liter Erlenmeyer flask is charged with sufficient sodium bicarbonate to cover the bottom of the flask and is placed into a dry ice-isopropanol bath. The reaction mixture is then poured slowly over the sodium bicarbonate to minimize foaming. Additional sodium bicarbonate is added until all foaming ceases. The neutralized mixture is treated with 200 ml of water and quickly extracted with 100 ml of methylene chloride. The organic solution so obtained is dried and concentrated to provide 39.5 grams of an oil. The oil is distilled under vacuum to provide a first cut taken at 73°–80° C at 57 mm Hg and a second cut at 80°–83° C at the same pressure.

The 25 ml of the second portion is dissolved in 100 ml of ethyl ether and extracted four times with 5 ml of 5% aqueous sodium hydroxide to remove the pink color. The basic fraction so obtained is acidified with 11.2 cc of hydrochloric acid and extracted twice with 10 ml of ethyl ether, dried over sodium sulfate, and concentrated.

This concentrate is then chromatographed to separate the 2-methylfuran-3-thiol and 2-methyl-[4,5H]dihydrofuran-3-thiol produced. These thiols have a roast meat aroma with the aroma of the furan-3-thiol being very similar to that of the disulfide produced in Example III.

The analytical data on the 2-methylfuran-3-thiol are:

| Infra-red: | |
|---|---|
| λmax | Interpretation |
| 3.92 | S—H group conjugated with aromatic ring |

-continued

| | |
|---|---|
| 7.40, 6.60 | Aromatic ring C=C bond |
| 7.26 | Methyl group |
| 13.58 | C—H bond of aromatic ring |

Proton Magnetic Resonance:
In carbon tetrachloride:
 2.12 (doublet, 3 protons),
 2.23 (doublet, 1 proton),
 6.08 (doublet, 1 proton) and
 7.04 ppm (doublet, 1 proton).
Mass Spectrum:
Base Peak 43, Molecular Peak 114. Other peaks in descending order: 41, 45, 85, 47, 113, 71, 75, 74.

EXAMPLE V

Preparation of bis(2-methyl-3-furyl) disulfide

The thiol produced in Example III is oxidized under mild conditions by dissolving 5 g of the thiol in 100 cc of hexane. The solution is placed in a 250 cc flask equipped with a sparger supplied by an air source, a stirrer, and a heater. Air is bubbled in at room temperature at a rate of 20 ml/minute during 20 hours. Solvent is replaced as required in order to maintain the original volume of solution. At the end of the reaction period the solvent is flash-evaporated and the resulting mixture is purified by column chromatography to yield 3 g of bis(2-methyl-3-furyl) disulfide.

The purified bis(2-methyl-3-furyl) disulfide has a full meat flavor and a cooked meat aroma when used in soup base at a concentration of 0.2 ppm. In a comparison 5-methyl-2-furyl disulfide is also used in soup base at a concentration of 0.2 ppm and is found to have only a chemical, rubbery taste and aroma.

The analytical data for the 3-furyl disulfide follow:

| Infra-red | |
|---|---|
| λmax | Interpretation |
| 3.22 | Aromatic C—H stretch |
| 6.32, 6.60 | Aromatic C=C stretch |
| 7.22 | Methyl group |
| 11.28 | Furanic ring vibration |
| 13.6 | C—H out-of-plane bend of a 2,3-disubstituted furan. |

Proton Magnetic Resonance
In carbon tetrachloride:
 7.14 (doublet, 2 protons),
 6.25 (doublet, 2 protons), and
 2.07 ppm (singlet, 6 protons).
Mass Spectrum
Base Peak 113; Molecular Peak 226; Other peaks in descending order: 43, 45, 51, 114, 85.

EXAMPLE VI

The following ingredients are homogeneously admixed at 25° C:

| Ingredient | Amount (g) |
|---|---|
| 2-Methylfuran-3-thiol | 2.0 |
| 2-Methyl-[4,5-H]-dihydrofuran-3-thiol | 0.5 |
| bis(2-Methyl-3-furyl) disulfide | 93.0 |
| bis(2-Methyl-3-furyl) monosulfide | 4.0 |
| bis(2-Methyl-3-furyl) trisulfide | 0.5 |

The mixture has an excellent roasted-meat flavor when used in a soup base at 10 ppm.

EXAMPLE VII

The monosulfide prepared in Example I is dissolved in propylene glycol to provide a 0.1% solution. This solution in the amount of 0.966 g is added to 7.3 g of a soup base consisting of:

| Ingredient | Amount (Parts/100 total) |
|---|---|
| Fine ground sodium chloride | 35.62 |
| Hydrolyzed vegetable protein | 27.40 |
| Monosodium glutamate | 17.81 |
| Sucrose | 10.96 |
| Beef fat | 5.48 |
| Sethness caramel color (powder B & C) | 2.73 |

The resulting mixture is added to 12 ounces of boiling water to obtain a soup having an excellent meat flavor.

The composition of Example VI (.005 g) when added to the above soup base also provides a soup having a good roasted-meat flavor. Similar results are obtained when the bis(2-ethyl-3-furyl) sulfide or bis(2-propyl-3-furyl) disulfide is used.

EXAMPLE VIII

One-half gram of the soup base mixture of Example VII is emulsified in a solution containing 100 g gum arabic and 300 g water. The resultant emulsion is spray-dried with a Bowen Lab Model Drier utilizing 250 cfs of air with an inlet temperature of 500° F, an outlet temperature of 200° F, and a wheel speed of 50,000 RPM.

Twelve grams of the spray-dried material is mixed with 29.2 g of the soup base set forth in Example VII. The resulting mixture is then added to 12 ounces of boiling water, and an excellent roasted-meat flavored soup is obtained.

EXAMPLE IX

The following ingredients are selected and mixed as described in Example VI to yield compositions having excellent meat flavor:

| Ingredient | Amount (Parts/100 total) |
|---|---|
| MIXTURE A | |
| 2-Methylfuran-3-thiol | 5. |
| 2-Methyl-3-thio[4,5H]-dihydrofuran | 5. |
| bis(2-Methyl-3-furyl) disulfide | 1. |
| bis(2-Methyl-3-furyl) monosulfide | 89. |
| MIXTURE B | |
| bis(2-Methyl-3-furyl) trisulfide | 15. |
| bis(4-Methyl-3-furyl) trisulfide | 5. |
| bis(4-Propyl-[4,5H]-dihydro-3-furyl) monosulfide | 5. |
| bis(2,5-Dimethyl-3-furyl) monosulfide | 25. |
| Corn oil | 50. |
| MIXTURE C | |
| 2-Ethylfuran-3-thiol | 9. |
| 2-Butylfuran-3-thiol | 9. |
| bis(2-Pentyl-3-furyl) trisulfide | 30. |
| bis(2-Ethyl-5-isopropyl-[2,3H]-dihydro-3-furyl) trisulfide | 1. |
| bis(2-Butyltetrahydro-3-furyl) monosulfide | 1. |
| Gum arabic | 50. |

EXAMPLE X

Isolation of bis(Furyl) Disulfides from a Reaction Mixture

A 4,000-pound batch having the following composition:

| | |
|---|---|
| Thiamine hydrochloride | 8.8 parts |
| L-Cysteine hydrochloride | 8.8 parts |
| Maggi 4 BE protein hydrolysate | 309.6 parts |
| Water | 672.8 parts |
| | 1,000.0 parts | is heated at reflux for 4 hours. After the first 45 minutes of reflux a total of 40 gallons of condensate is removed uniformly over the next 3 hours and 15 minutes. Each gallon of condensate is extracted with 400 ml portions of methylene chloride. After removal of the methylene chloride under very mild vacuum, a 50 ml residue is obtained which possesses an extremely powerful roast-meat aroma.

Preparative thin-layer chromatography (8×8"× 1.25 mm, silica-gel G, 200 λ/plate) of approximately 2.4 g gave 0.066 g of a pure compound having a good basic roast-meat aroma upon proper dilution. The mass spectrum of this compound is as follows: m/c (rel. intensity) 226 (9.6), 227 (1.9), 228 (1.7), 113 (10.0), 43 (4.7), 114 (4.4), 45 (3.6), 85 (3.1), 51 (2.9), 69 (17.6). Proton magnetic resonance in carbon tetrachloride shows 2.07 (singlet,

6.25 (doublet, 2 furyl protons), and 7.14 (doublet, 2 furyl protons).

The above data are in excellent agreement with the proposed structure of bis(2-methyl-3-furyl) disulfide:

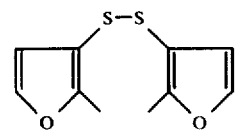

When the crude extract is analyzed by preparative gas/liquid chromatography a compound having a very intense pot roast odor is obtained. This compound has been identified as 2-methyl-furan-3-thiol.

EXAMPLE XI

Preparation of 2-Methyl-3-Furanthiol

A 500 cc three-neck round-bottom flask is fitted with a Y-tube, thermometer, and stirrer and is then charged with 32 g of fuming sulfuric acid (oleum) containing 20% $SO_3$. The temperature is maintained at 24°–28° C, and 40 g (0.318 mol) of 5-methyl-2-furoic acid is slowly added to the oleum during a period of 45 minutes. After addition is complete, the reaction mixture is stirred for an additional 2 ¼ hours and then held for 16 hours.

The reaction mixture is thereupon poured over 600 cc of ice-water mixture and neutralized to pH 5 with 430 g of barium carbonate, during which neutralization a thick paste forms. After addition of 500 cc of water, the paste is boiled and then vacuum-filtered while hot. The barium sulfate-containing solids which remain after filtration are boiled with 700 cc of water, and the mixture is vacuum-filtered while hot. Both filtrates are combined and refrigerated for two days to form crystals which are recovered. The filtrate is evaporated to a volume of about 500 cc and cooled in ice to recover further crystals. The remaining filtrate is evaporated to a volume of 50 cc, 100 cc of methanol is added, and the liquid is chilled to obtain crystals. The yield of solids (barium-2-methyl-3-sulfo-5-furoic acid) from the three crystallizations is 93.5 g.

Barium-2-methyl-3-sulfo-5-furoic acid in the amount of 98.2 g and 1800 cc of distilled water is charged to a flask, and the flask is heated in a steam bath to 70° C until all the solids are dissolved. Then, 116 g of 20% aqueous sulfuric acid is gradually added to precipitate barium sulfate. The decanted liquid is cooled in ice and filtered. The water is evaporated from the filtrate, and the remainder is evaporated under high vacuum at room temperature to obtain 35.1 g of yellow oil which crystallizes after being held in a desiccator overnight.

The sodium salt of the sulfo furoic acid is prepared by dissolving 33.1 g of the crystallized oil (sulfo furoic acid) in 100 cc of water and gradually adding 6.75 g of sodium bicarbonate. After drying in a steam bath and then in a vacuum desiccator, 37.4 g of the sodium salt containing water of crystallization is obtained.

The sodium salt is decarboxylated by charging 13.2 g of mercuric chloride ($HgCl_2$) in 60 cc of water to a 500 cc three-neck round-bottom flask fitted with a condenser having a gas outlet and with a Y-tube, a nitrogen inlet, a stirrer, and a heating mantle. Then 11.1 g of the sulfo furoic acid sodium salt in 80 cc of water is charged to the flask, and this is followed by 1.95 g of sodium hydroxide in 20 cc of water. The mixture is refluxed for 2 hours and 40 minutes while the pH is maintained at 4-5 by addition of aqueous sodium hydroxide or hydrochloric acid as required, and carbon dioxide evolves. The mixture is then cooled to room temperature and filtered. The filtrate is adjusted to pH 7-8 with 10% aqueous sodium bicarbonate, and hydrogen sulfide is bubbled through the mixture to precipitate mercuric sulfide. The mercuric sulfide is separated by filtration and the filtrate is concentrated in a rotary evaporator. About 30 cc of water is added to dissolve all the solids after concentration and the mixture is cooled to crystallize out 4.93 g of 2-methyl furan-3-sulfonic material. The crystals are filtered from the supernatant and dried.

The sulfonic acid derivative is converted to the sulfonyl chloride derivative by treatment of 1.3 g of the sulfonic acid with 33 g of thionyl chloride and two drops of dimethyl formamide for 75 minutes at 25° C. The excess thionyl chloride is removed on a rotary evaporator, the residue is washed with benzene, and the benzene is stripped off to obtain 0.88 g of amber oil having a sharp, meaty odor.

The amber oil so obtained is then reacted with 0.8 g of lithium aluminum hydride in 30 cc of diethyl ether. The reaction is carried out by adding the hydride to 20 cc of ether, filtering, adding the oil in 10 cc of ether at reflux during a period of 8 minutes. The reflux is then continued for 75 minutes. After reflux the remaining hydride in the mixture is reacted with methanol in ether, and the product so obtained is poured into ice water, acidified to pH 1 with hydrochloric acid, and extracted with ether to obtain an oil. This oil is dried, filtered, and stripped of ether to obtain 0.27 g of a yellow oil having a good meaty aroma.

Proton magnetic resonance of the major peak obtained from this oil by gas-liquid chromatography shows a thiol. Mass spectroscopy of this material shows peaks at 114 and 113. These results confirm the production of the 2-methyl-3-furanthiol.

EXAMPLE XII

Preparation of bis-(2-methyl-3-furyl) tetrasulfide

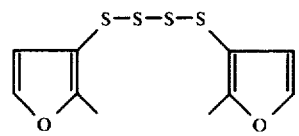

To a flask containing a solution of 2-methyl-3-furanthiol (1.65 g) in ethyl ether (10 ml.) and solid sodium bicarbonate (3.0 g) cooled to −30° C was added dropwise a solution of sulfur monochloride (1.01 g) in ethyl ether (10 ml). After standing 45 minutes the reaction mixture is poured into water (75 ml), the upper layer is separated and washed with water (25 ml). After back-extracting the aqueous washings with ethyl ether (25 ml.) the ether solutions are combined and washed with water (2 × 30 ml.) until the pH of the wash is about 5. Drying the ether solution with anhydrous sodium sulfate followed by solvent removal in vacuo gives 1.6 g. of crude bis(2-methyl-3-furyl) tetrasulfide.

Column chromatography of the amber oil on 60 g. of silicic acid packed in hexane followed by elution with hexane gives 1.1 g. of analytically pure bis(2-methyl-3-furyl) tetrasulfide as a light yellow oil. The purified bis(2-methyl-3-furyl) tetrasulfide has a full meat flavor and brothiness when used in soup base at a concentration of 0.2 ppm.

Infra-red

λmax 3100
2900
1570
1510
1435
1380
122.5
1122
1086
938
887
730
645 cm$^{-1}$

Proton Magnetic Resonance in carbon tetrachloride.

2.37 (singlet, 6 protons)
6.38 (doublet, J=2Hz, 2 protons)
7.20 (doublet, J=2Hz, 2 protons)

Mass Spectrum

Base Peak 43; Molecular Peak 290. Other peaks in descending order 113, 45, 226, 114, 51, 85, 69.

Elemental Analysis: Calculated for $C_{10}H_{10}O_2S_4$; C, 41.35; H, 3.47; S, 44.16. Found: C, 41.52; H, 3.38; S, 43.77.

EXAMPLE XIII

The following ingredients are homogeneously admixed at 25° C:

| Ingredient | Amount (g.) |
|---|---|
| 2-Ethylfuran-3-thiol | 9 |
| 2-Butylfuran-3-thiol | 9 |
| bis (2-Pentyl-3-furyl)trisulfide | 30 |
| bis (2-Ethyl-5-isopropyl-[2,3H]-dihydro-3-furyl)trisulfide | 1 |
| bis (2-Butyltetrahydro-3-furyl) monosulfide | 1 |
| bis (2-Methyl-3-furyl) tetrasulfide | 5 |
| Gum arabic | 45 |
| Total | 100 |

The mixture has an excellent roasted-meat flavor and may be added to a soup base at 10 ppm.

What is claimed is:

1. A furan derivative having the formula

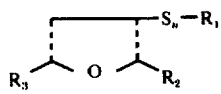

wherein $R_3$ is hydrogen or lower alkyl of one to five carbon atoms, and:
  (1) $n$ is one, two, three or four and $R_1$ is moiety of the formula

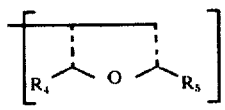

wherein $R_4$ is the same as $R_2$ and $R_5$ is the same as $R_3$ wherein each dashed line represents a single or double bond and the dashed line adjacent to $R_4$ has the same value as the dashed line adjacent to $R_2$ and the dashed line adjacent to $R_5$ has the same value as the dashed line adjacent to $R_3$, $R_2$ is lower alkyl of from two to five carbon atoms when $n$ is two and $R_2$ is alkyl of from one to five carbon atoms when $n$ is one, three, or four; or
  (2) $n$ is two or three, each dashed line is a single or double bond, and $R_1$ and $R_2$ are lower alkyl containing from one to five carbon atoms and provided that when $n$ is two and $R_1$ and $R_2$ are methyl the dashed lines are not both double bonds.

2. bis(2,5-Dimethyl-3-furyl) sulfide.
3. bis(2,5-Dimethyl-3-furyl) disulfide.
4. A process for the production of furan derivatives which comprises reacting a 2,5-dialkylfuran with sulfur monochloride or sulfur dichloride and forming bis(2,5-dialkyl-3-furyl) sulfide or bis(2,5-dialkyl-3-furyl) disulfide.
5. bis(2-Methyl-3-furyl) tetrasulfide.
6. Bis(2-methyl-3-furyl)trisulfide.
7. A substantially pure form of methyl(2-methyl-3-furyl)disulfide.
8. Methyl(2-methyl-3-furyl)trisulfide.
9. Substantially pure bis(2-methyl-3-furyl)disulfide having a λ max at 3.22, 6.32, 6.60, 7.22, 11.28 and 13.6 μ by infrared spectroscopy.

* * * * *